United States Patent
Strömmer

[19]

[11] Patent Number: 5,872,364
[45] Date of Patent: Feb. 16, 1999

[54] METHOD AND APPARATUS SUITABLE FOR USE AS A SENSOR SYSTEM IN A CAMERA HEAD INTENDED FOR DIGITAL IMAGING

[75] Inventor: Pekka Strömmer, Espoo, Finland

[73] Assignee: Planmed Oy, Helsinki, Finland

[21] Appl. No.: 752,583

[22] Filed: Nov. 21, 1996

[30] Foreign Application Priority Data

Nov. 21, 1995 [FI] Finland ..................... 955599

[51] Int. Cl.⁶ ................. G01T 1/29; G01T 1/20
[52] U.S. Cl. .............. 250/370.09; 250/366; 250/368; 250/370.11; 250/208.1
[58] Field of Search .............. 250/370.09, 370.11, 250/208.1, 370.08, 366, 367, 368; 378/37, 38

[56] References Cited

U.S. PATENT DOCUMENTS

| | | |
|---|---|---|
| 4,323,925 | 4/1982 | Abell et al. . |
| 4,543,490 | 9/1985 | Gupta ............................ 250/370.11 |
| 4,810,881 | 3/1989 | Berger et al. ................. 250/370.09 |
| 4,931,647 | 6/1990 | Hiruma et al. ............... 250/368 |
| 5,065,245 | 11/1991 | Carnall, Jr. et al. ........ 250/208.1 |
| 5,159,455 | 10/1992 | Cox et al. . |
| 5,550,380 | 8/1996 | Sugawara et al. ............. 250/370.09 |

FOREIGN PATENT DOCUMENTS

| | | |
|---|---|---|
| 0 262 267 | 4/1986 | European Pat. Off. . |
| 0 286 393 | 10/1988 | European Pat. Off. . |
| 0 576 735 A1 | 1/1994 | European Pat. Off. . |
| 39 32 845 A | 4/1991 | Germany . |

*Primary Examiner*—Edward J. Glick
*Attorney, Agent, or Firm*—Jones & Askew

[57] ABSTRACT

The invention relates to a method and apparatus for constructing a sensor system (100) sensitive to electromagnetic radiation for use in a digital imaging camera head. The sensor system (100) is capable of delivering an electrical signal containing the image information formed by electromagnetic radiation incident on the sensor system (100). The sensor system (100) is comprised of a number (N pcs.) of mutually essentially identical modular sensor units ($10_1 \ldots 10_N$) and of an equal number (N pcs.) of mutually essentially identical modular control electronics units ($20_1 \ldots 20_N$) suited for the control and signal processing of said sensor units ($10_1 \ldots 10_N$). The sensor system (100) has a modular design permitting the dimensions of the imaging area covered by the sensor system (100) to be expanded or reduced as required for the needs of an imaging application by adding or reducing, respectively, the number of the modular sensor units (10,20). Each individual modular sensor unit (10) and/or control electronics unit (20) are/is also separately removable for servicing.

10 Claims, 5 Drawing Sheets

METHOD AND APPARATUS SUITABLE FOR USE AS A SENSOR SYSTEM IN A CAMERA HEAD INTENDED FOR DIGITAL IMAGING

BACKGROUND OF THE INVENTION

The present invention relates to a method of constructing a sensor system which is sensitive to electromagnetic radiation and is suitable for use in a digital imaging camera head, said sensor system delivering an electrical signal containing the image information formed by electromagnetic radiation incident on the sensor system.

The invention also concerns a solid-state sensor system of a CCD camera head intended for digital imaging, said sensor system comprising a radiation-responsive detector element array with control electronics connected thereto and an interface unit by which the sensor system is connected to an image recording apparatus, and said sensor system further comprising a frame unit, on which the sensor system is adapted.

The present invention relates broadly to object imaging by means of electromagnetic radiation. In particular, the invention is related to digital imaging utilizing CCD sensor systems.

The method and apparatus according to the invention are intended broadly for digital imaging and particularly for medical x-ray imaging such as panoramic dental radiography and mammography.

Conventionally, digital imaging is also used in medical x-ray technology, wherein it has certain indisputable benefits over the use of radiation-sensitive film requiring a development process. Such benefits are those related to viewing, handling, storage and remote transfer of digitally imaged and stored picture information which in the future will be further accentuated when the medical services and hospital systems will increasingly move into digital techniques in general and particularly in the processing of x-ray images and similar information. Hence, it is one of the principal objects of the present invention to bring an essential advancement to this on-going trend.

As to their basic structure, solid-state sensors intended for digital imaging comprise small radiation-sensitive detector elements called pixels arranged into larger planar arrays, or in a simplified form, into a single-row line sensor. Electromagnetic radiation such as light, infra-red radiation or x-rays absorbed at the area of the detector elements generates an electrical charge in the elements with a magnitude dependent on the intensity of absorbed radiation (that is, flux density and energy of absorbed quanta) of impinging radiation. Here, the magnitude of the electrical charges grows as a function of time, which means that during the exposure time, the detector element integrates the charge generated by the radiation impinging over the sensor area, thus in principle giving a possibility of controlling the magnitude of the detector element output signal through varying the integration time.

In the prior art, CCD (Charge-Coupled Device) image sensors and their control electronics were designed and optimized always separately for a certain application and specific use, whereby such conventional image sensor systems are ill fit for other applications no matter how similar. The development of new types of CCD sensors is extremely expensive and time-consuming. Typically, a new type of CCD sensor takes at least a year or more involving an R&D budget of at least USD 1 million. Correspondingly, the development of control electronics for such a new CCD sensor takes about the same time, raising the system R&D costs by at least about USD 250,000. Given these facts, it is obvious that since the development of a new CCD sensor type presumes a practical application with a commercial potential of development cost payback in a reasonable time, applications using small quantities of CCD sensors cannot be implemented in practice within the constraints of a reasonable cost budget. On the other hand, while new CCD sensors are continually developed for applications of reasonably high volume, even in such projects the proportion of costs attributed to the CCD sensors rises relatively high when conventional techniques are used.

A single solid-state sensor chip, particularly a CCD sensor, made by concurrent technology has such a small active area that any larger image area cannot be recorded by means of a single sensor, particularly when reasonably or extremely high requirements are set for the sensor sensitivity as is the case in x-ray imaging. Resultingly, a number of CCD sensor chips with control circuit blocks are necessary in the construction of a complete digital camera head.

As known in the art, digital camera heads with their image sensors and control circuitry are generally designed for a certain application, which makes them unsuitable for modification or adaptation to any other application whether similar or not. For example, with the help of time-delayed integration (TDI) technique, applications can be found in, e.g., mammography or panoramic x-ray imaging of dental or skull areas in which a single basic construction of the imaging apparatus is produced in modified versions for these applications that differ from each other chiefly by the active area of the imaging sensor only. In mammography equipment, the length of the scanning CCD line sensor typically is either 18 cm or 24 cm, depending on whether image areas of 18×24 cm or 24×30 cm are being recorded. In panoramic imaging equipment, the length of the scanning CCD line sensor typically is approx 14 cm for panoramic imaging alone and 18 cm or 24 cm for different modes of skull imaging.

Today, the purchase decision of a digital CCD camera head must be based on knowledge covering all possible future applications, thus assuring the suitability of the purchased equipment version for all of them, because retrofitting of a camera head implemented by means of conventional technology is not either possible, or if possible, requires a complete replacement of the CCD camera head with another type, which obviously is an uneconomical operation. On the other hand, the purchase of a CCD camera head with an imaging area covering the maximum size required by any conceivable application is impractical, because the price of this type of imaging system is chiefly determined by the CCD sensor assembly itself and its control electronics, whereby the equipment price can easily double from the inclusion of a provision covering all possible future imaging needs that may well remain unrealized.

Another problem related to conventional digital CCD camera head systems is servicing of the equipment. When even a slight malfunction occurs the CCD sensor of the equipment or its control electronics, the sensor must be replaced as a whole unit, which by its servicing cost rises close to the purchase price of new camera head. If fabricated by conventional techniques, an integrally bonded CCD sensor package must always be replaced as a whole unit even if only a small component actually fails therein. Similarly, the control electronics of the imaging system have conventionally been designed and traditionally built for the entire sensor package, whereby its malfunction has also required the replacement of the entire electronics package.

SUMMARY OF THE INVENTION

It is a broad object of the present invention to further develop the sensor systems of digital camera heads, particularly those based on CCD sensors, so that the above-discussed problems are extensively solved and the drawbacks eliminated.

It is a particular object of the present invention to achieve such a sensor system suited for medical x-ray imaging, particularly mammography and panoramic dental or skull radiography, that offers improved flexibility in its realization and higher cost-efficiency so that different imaging modes and later needs for wider imaging areas can be implemented with a higher economy and lower investment costs over those possible through conventional techniques.

It is a further particular object of the present invention to achieve such a CCD sensor system, particularly suited for medical x-ray technology, that offers simplified and more economical servicing combined with a significantly reduced number of spare parts and costs over the prior art To achieve the above-stated goals of the invention and others to be explained later, the method according to the invention is principally characterized in that the sensor system is comprised of a number of mutually essentially identical modular sensor units and of an equal number of mutually essentially identical modular control electronics units suited for the control and signal processing of said sensor units, and that the modularity of the sensor system is adapted and arranged so that the dimensions of the imaging area covered by the sensor system can be expanded or reduced by adding or reducing, respectively, the number of the modular sensor units, and that each individual modular sensor unit and/or control electronics unit is also separately removable for servicing.

Furthermore, the apparatus according to the invention is principally characterized in that the solid-state sensor system is designed into a modular system comprised of a number of mutually essentially identical modular CCD sensor units and of an equal number of mutually essentially identical modular control electronics units, each being connected to its respective modular sensor unit, and that said sensor system incorporates a base unit for said modular sensor unit, whereby said modular sensor units can be added, removed or replaced as necessary for expanding or reducing of the imaging area of said sensor system and servicing the system.

The sensor system according to the invention has a modular construction that can be expanded or reduced as required by imaging needs in an economically advantageous manner through simple and rapid operations. Additionally, the invention offers benefits related to servicing of the sensor system, since the modular structure of the sensor units permits replacement of a malfunctioning modular unit alone, that is, a modular sensor unit and/or its control electronics unit can be changed without the need for replacing the entire CCD sensor system with its dedicated control electronics. Other effects and advantages of the invention will become evident from the description below.

In the following the invention will be examined in greater detail by making reference to the diagrams of appended drawings illustrating diagrammatically a few exemplifying embodiments of the invention, whereby the details of the diagrams must not be understood as limiting the scope of the invention, in which drawings

DETAILED DESCRIPTION OF PREFERRED EMBODIMENT

Figure 1:
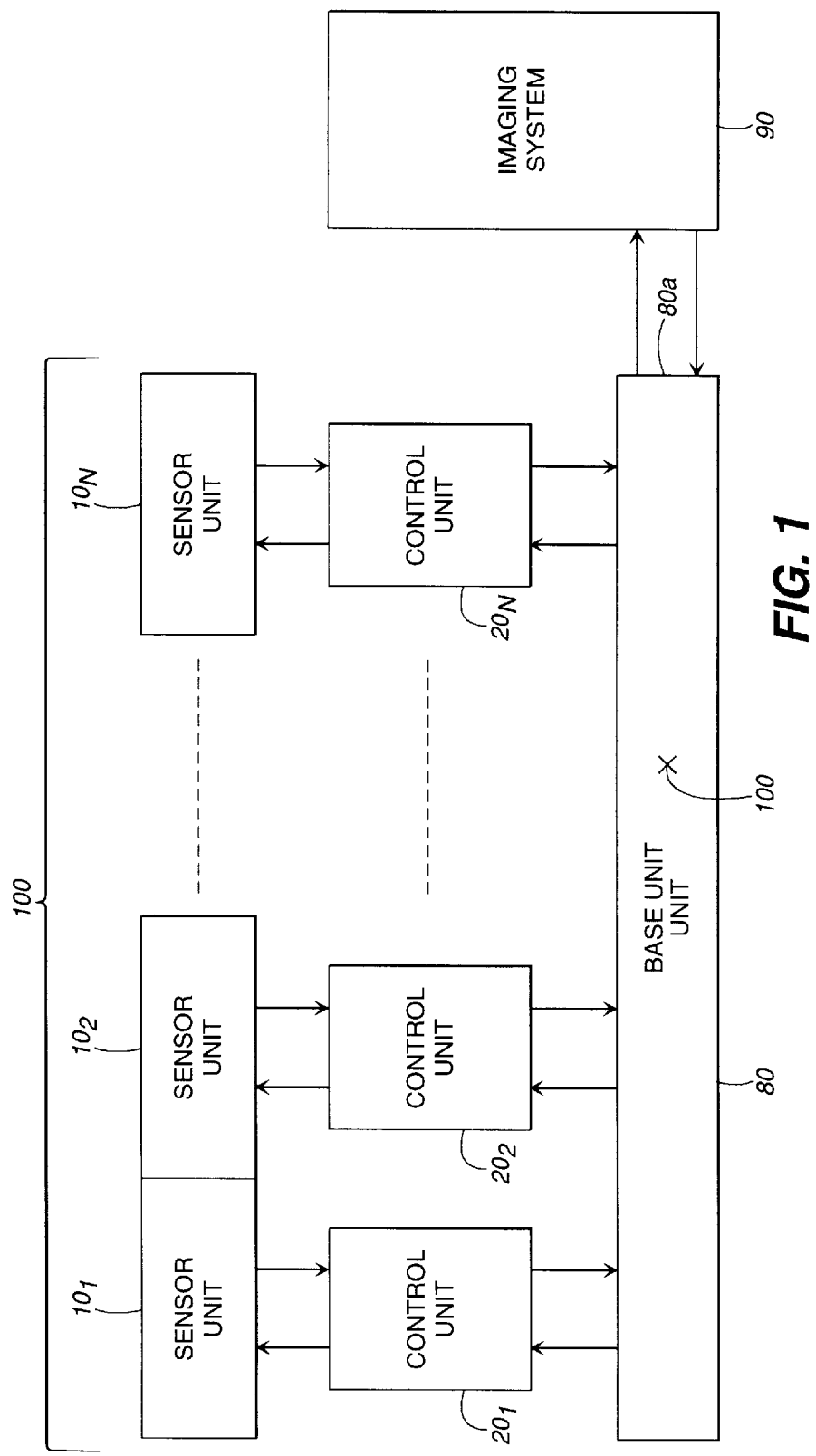
FIG. 1 is a schematic block diagram of a sensor system according to the invention.

Referring to FIG. 1, a sensor system 100 according to the invention may have, e.g., such a structure as is diagrammatically shown therein. Here, the sensor system 100 is assembled from a required number of modular solid-state sensor units $10_1 \ldots 10_N$, each of which is connected to its dedicated modular control electronics unit $20_1 \ldots 20_N$, whose number N thus is equal to that of the sensor units 10. The control electronics units are in turn attached to a common base unit 80 having an uncomplicated construction serving to interface the sensor system 100 to an imaging system 90 proper. With varying sizes of the sensor system, the imaging system 90 with the common base unit 80 remain unchanged and the dimensions of the imaging area required in each application can be set by selecting a proper number N of the modular sensor units 10 and their respective modular control electronics units 20. The base unit 80 is already initially made so wide that it as such permits maximal expansion of the sensor system 100. Alternatively, retrofit expansion of the sensor system can be made by attaching a second base unit 80 adjacent to the first one.

Figure 2:
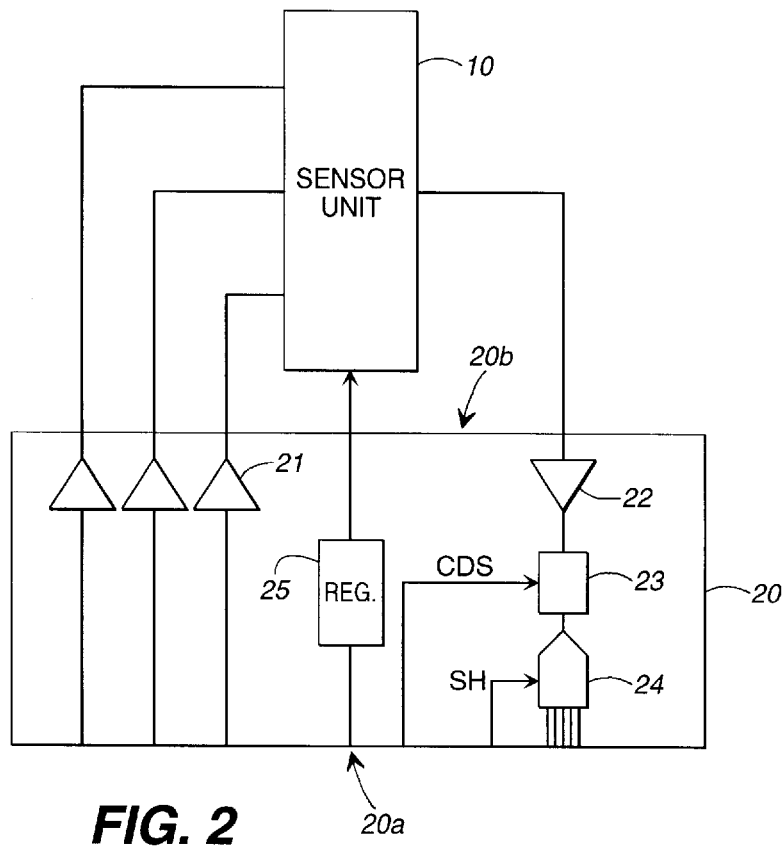
FIG. 2 is a more detailed block diagram of a modular control electronics unit for one modular sensor unit.

Referring to FIG. 2, the modular control electronics unit 20 for one modular sensor unit 10 is shown in a detailed block diagram. The control electronics unit 20 is connected by the upper signal lines 20b to the sensor unit 10 and by the lower signal lines 20a to the base unit 80 (shown in FIGS. 1 and 3). The control electronics unit 20 contains all elements necessary for controlling one sensor unit 10 such as control signal buffer stages 21, voltage regulator 25 of the supply voltages required by the sensor unit, sensor unit output voltage amplifier 22, a correlated double sampling CDS circuit 23 required for interfacing CCD sensors and an analog/digital converter 24 for the output signals.

Figure 3:
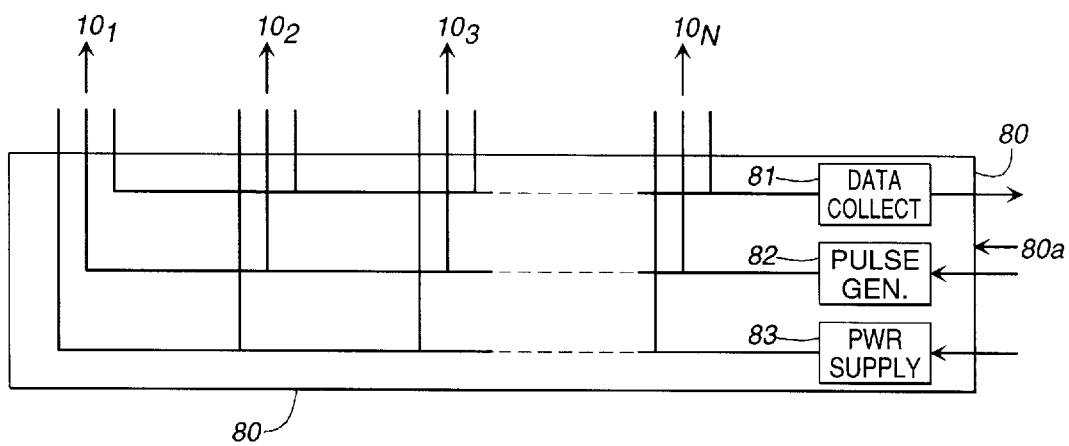
FIG. 3 is a block diagram of a base unit common to all modular units of a sensor system.

Referring to FIG. 3, therein is shown the configuration of a base unit 80 common to the modular sensor and control electronics units $10_1 \ldots 10_N, 20_1 \ldots 20_N$. The base unit 80 is connected by its right side signal lines 80a to an imaging apparatus 90, wherefrom the base unit 80 receives its supply voltages and synchronizing signals and whereto it delivers the image information retrieved from the modular sensor units $10_1 \ldots 10_N$. In FIG. 3, interfacing to the sensor system 100 is shown implemented so that a power supply 83 delivers the supply voltages to each sensor/control electronics unit pair 10,20, while a synchronizing pulse generator 82 provides the timing signals required for controlling said units. A data collection unit 81 receives the image information delivered by each sensor/control electronics unit pair 10,20 and forwards the information in processed form to the imaging apparatus 90.

Figure 4:
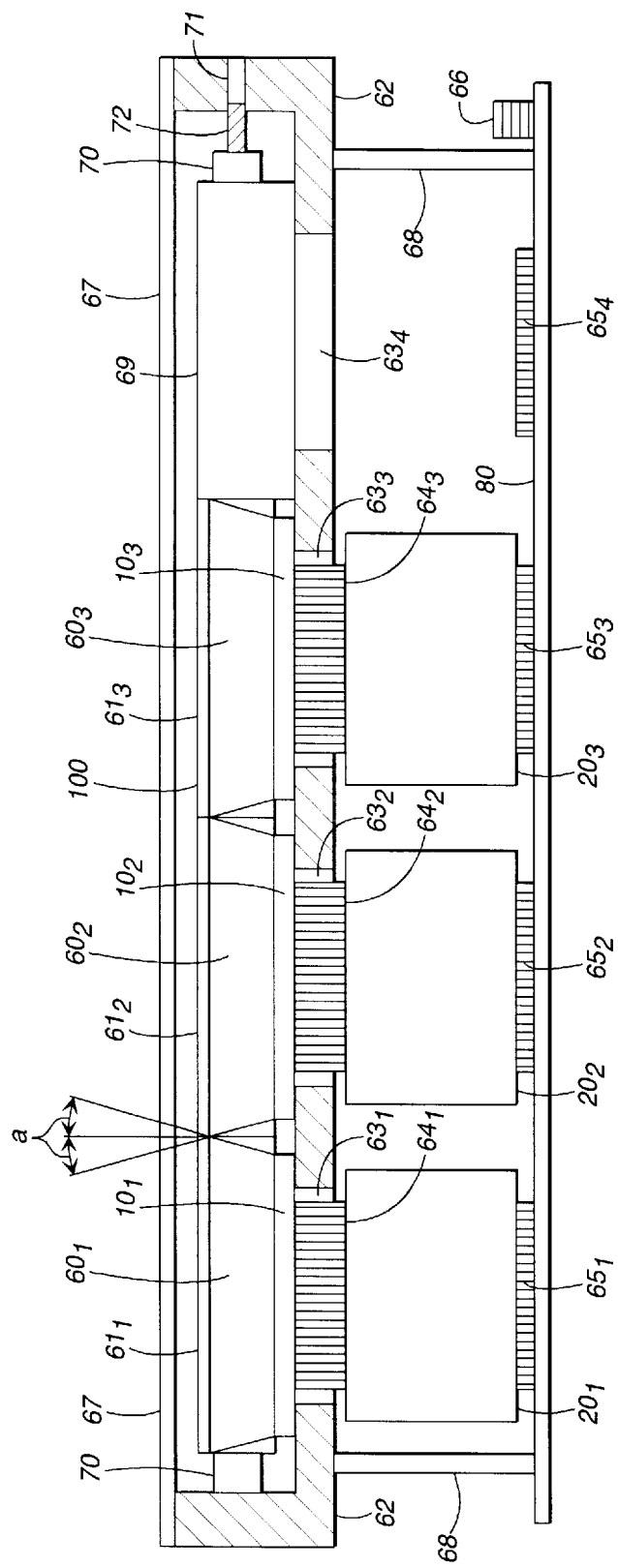
FIG. 4 is a sectional side view of an embodiment of a sensor system according to the invention taken along the longitudinal axis of the sensor assembly.
Figure 5:
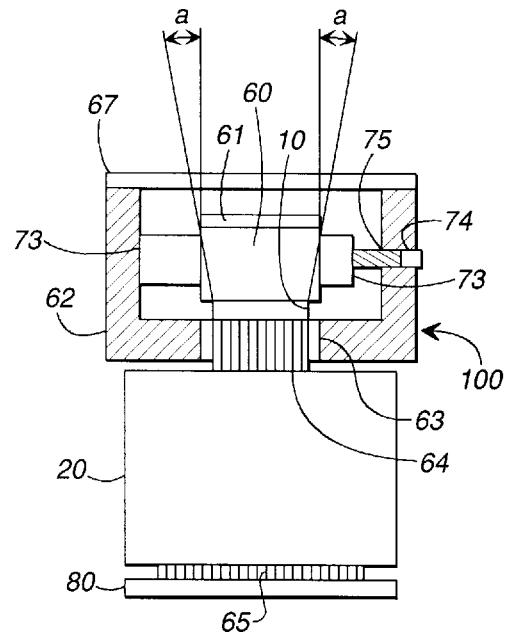
FIG. 5 shows a cross-sectional view of the assembly of FIG. 4, now taken along a plane perpendicular to the plane of the longitudinal section.

Referring to FIGS. 4 and 5, an assembled sensor system is comprised of modular CCD sensor units $10_1 \ldots 10_3$ with optical fibers $60_1 \ldots 60_3$ bonded at their lower ends with an adhesive to the detector element and having a scintillation material layer $61_1 \ldots 61_3$ at their upper ends. Each sensor unit $10_1 \ldots 10_3$ connected to its dedicated control electronics unit $20_1 \ldots 20_3$ via a connector $64_1 \ldots 64_3$ located in a hole $63_1 \ldots 63_3$ made to the frame 62, whereby the contact pins of the sensor unit $10_1 \ldots 10_3$ are aligned for insertion into the connectors. Correspondingly, the modular control electronics units $20_1 \ldots 20_3$ attached via connectors $65_1 \ldots 65_3$ to the common base unit 80 of the CCD camera head that further has a connector 66 for interfacing to an imaging apparatus 90. The sensor units 10 are mounted in place longitudinally end-to-end between clamp pieces 70 under a suitable compression imparted by a screw 71 and a spring 72. In the lateral direction, each sensor unit 10 is fixed between its own clamp pieces 73, tightened in place by means of screws 74 and a spring 75. By providing clamp pieces 73 on both sides of the set of modular sensor units 10 with an adjustment screw set or similar arrangement, the sensor unit set may be accurately aligned on a single line as required with the help of the clamping arrangement of the sensor units 10 shown in FIGS. 4 and 5. As the detector elements of the sensor units 10 are also responsive to visible light, they are enclosed in a dark space sealed with a protective cover 67 transparent to x-rays. The base unit 80 is attached to the frame 62 by means of standoffs 68.

In FIG. 4 is shown such an embodiment of the invention having the camera head provided with a facility for retrofit installation of a fourth sensor unit $10_4$. For this purpose, the support frame 62 is provided with an opening $63_4$ and a connector $64_4$ in the base unit 80. Initially, the extra sensor unit $10_4$ is replaced by a filler piece 69 having a thermal expansion coefficient essentially equal to that of the sensor units $10_1 \ldots 10_3$.

Thus, any of the sensor units $10_1 \ldots 10_3$ can be replaced simply by untightening the fixing screws 71 and 74 and removing the cover 67. Thence, the filler piece 69 may be replaced by an extra sensor unit $10_4, 20_4$, or alternatively, any redundant sensor unit 10 may be replaced by a second filler piece 69. Similarly, any of the sensor-unit-specific control electronics units 20 may be replaced, added or removed through simply detaching the base unit 80.

The fibers of the optical fiber system 60 are tapered toward the detector elements, whereby a contiguous imaging area free from inter-unit borders can be achieved even in structures not having the active imaging area of the sensor units 10 extending up to the edges of the sensor units. In FIGS. 4 and 5, reference letter a denotes the taper angle of the optical fibers 10. The above-described advantageous embodiment of a sensor system assembled using the method according to the invention is such that has a scanning sensor with a length corresponding to the active imaging area width scanned by the sensor head, whereby the width of the imaging area is set by the length of the scanning motion of the sensor head. When adapting the invention to such scanning sensor heads, concurrently also the TDI (Time Delayed Integration) imaging principle is used that is known in the art and is explained in more detail in FI Patent Application No. FI 955,595 (U.S. application Ser. No. 08/754,524, filed by the applicant simultaneously with the present application.

Figure 6:
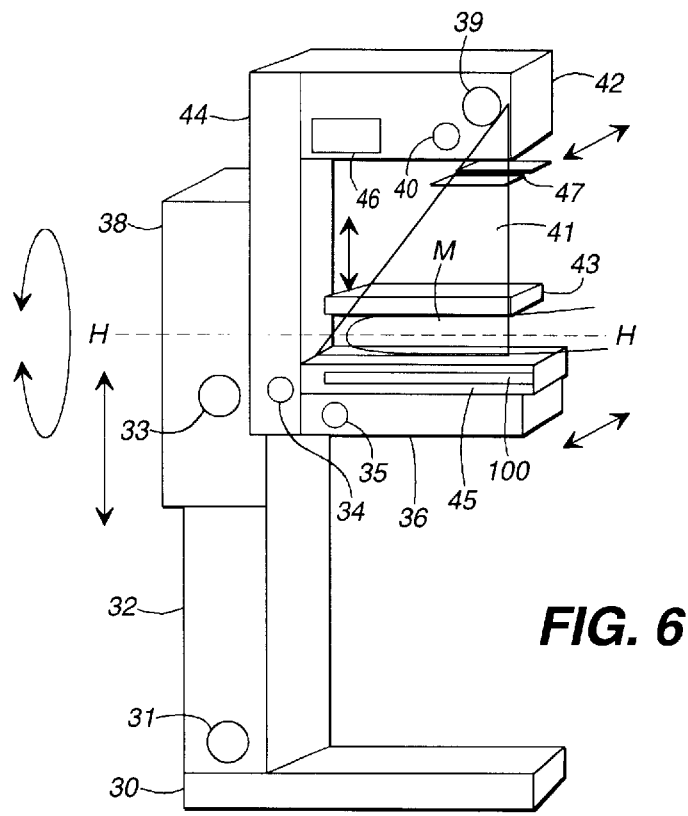
FIG. 6 is a perspective view of a mammography unit suitable for acting as an application platform for an embodiment of the invention.

Referring to FIG. 6, a mammography apparatus suited for use as an application platform for the present invention is shown therein standing on a base 30. To the base 30 is attached a fixed vertical column section 32 with a motor 31 inside the fixed section actuating a telescopically movable vertical column section 38. The vertical column houses a motor 33 for rotating a C-arm 44 about a horizontal axis H—H. One end of the C-arm supports an x-ray generator 42, while the other end of the arm carries a lower compression paddle 36 against which a breast M to be radiographed is compressed with the help of an upper compression paddle 43 actuated by a motor 34. During the exposure of the breast M, a narrow x-ray beam 41 emitted by an x-ray tube 39 passes through a primary blind 47, which is adapted laterally movable by means of a motor 40, then passes through the breast M being radiographed and finally is incident on a sensor head 45, which is adapted simultaneously movable with the primary blind by means of a motor 35 and comprises a CCD sensor system 100 having a modular construction of the above-described type according to the invention.

Figure 7:
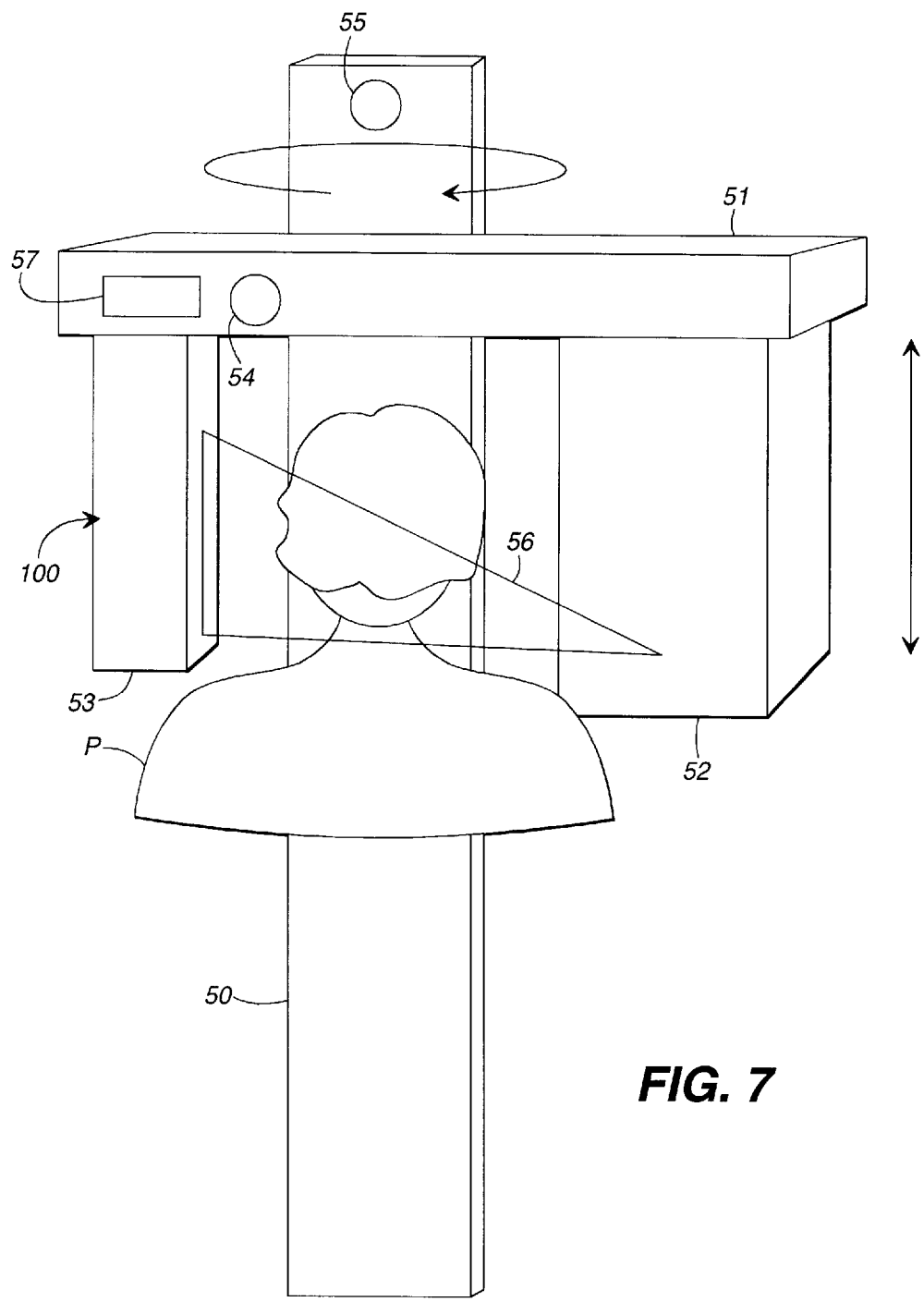
FIG. 7 is a perspective view of a panoramic dental x-ray apparatus suitable for acting as an application platform for an embodiment of the invention.

In FIG. 7 is shown a panoramic x-ray apparatus principally intended for dental radiography, comprised of a vertical column 50 carrying a horizontal support arm 51, adapted vertically movable by means of a motor 55 and rotatable by means of a motor 54, said horizontal support arm carrying at its one end an x-ray generator 52, whereby a narrow x-ray beam 56 emitted by the generator passes through the tissues of a patient P from one side and is on the other side incident on a sensor head 53 comprising a CCD sensor system 100 having a modular construction of the above-described type according to the invention.

In mammography, the invention can be utilized by first purchasing a CCD sensor system 100 equipped for imaging 18 by 24 cm areas only, and later, if so required, the sensor system 100 can be retrofitted for a larger imaging area of 24 by 30 cm. Similarly, in panoramic dental radiography a CCD sensor system 100 initially equipped for panoramic dental exposures only can be retrofitted for skull imaging in one or even several steps, e.g., first for the 18 cm image format and later for the 24 cm image format.

With regard to a detailed description of the modular sensor units 10 and the sensor system 100, reference is made to FI Patent Application No. FI 955,598, filed by the applicant simultaneously with the present application.

Not being limited by the above-described exemplifying embodiments, the details of the invention may be varied within the scope and inventive spirit of the annexed claims.

I claim:

1. A method of constructing a sensor system which is sensitive to electromagnetic radiation and is suitable for use in a digital imaging camera head, the sensor system delivering an electrical signal containing the image information formed by electromagnetic radiation incident on the sensor system, comprising the steps of:

arranging a plurality of mutually substantially identical modular sensor units to cover an imaging area of predetermined dimension, the imaging area being greater than an imaging area of an individual sensor unit, whereby the imaging area is expandable or reducible by adding or reducing the number of sensor units in the arranged sensor units;

providing an equal plurality of mutually substantially identical modular electronic control units each operatively associated with a corresponding sensor unit for control and signal processing of the sensor units; and making each sensor unit and each control unit separately removable from the arranged sensor units and corresponding control units, so that a problem in the sensor system can be serviced by replacing an individual unit without replacing the entire sensor system.

2. The method as in claim 1, wherein the sensor system is formed by mounting the sensor units end-to-end or adjacently in parallel so that an image formed by the sensor system is free from disturbing artifacts at inter-unit borders between adjacent modular sensor units.

3. The method as in claim 1, wherein said modular sensor units comprise CCD modular sensor units responsive to x-rays.

4. The method as in claim 1, wherein said modular sensor units are responsive to x-rays.

5. A solid-state sensor system suitable for use in a CCD digital imaging camera head, said sensor system comprising:

a modular array including a number (N) of mutually substantially identical modular CCD sensor units and an equal number (N) of mutually substantially identical modular control electronics units each of which is connected to a corresponding modular sensor unit for control and signal processing of the sensor units;

a base unit adapted for the assembly of said modular sensor units to cover an imaging area of selected area greater than the individual area of an individual sensor unit; and means assembling said modular sensor units and corresponding connected control units to the base unit so that each sensor unit and each connected control unit is removable from the imaging area separately from other sensor units and connected control units, whereby each said modular sensor unit and corresponding control unit can be added, removed, and replaced in the base unit as necessary for expanding or reducing the imaging area of said sensor system and for servicing the system.

6. The sensor system as defined in claim 5, wherein:

the modular CCD sensor units have optical fibers connected thereto; and outer end surfaces of the optical fibers are covered by a layer of scintillation material capable of converting image information conveyed by x-rays incident thereon into light in the visible range.

7. The sensor system as defined in claim 6, characterized in that the fibers of the sensor units are tapered with a tapering angle (a) toward the adjacent sensor unit in the sensor system, whereby the angled fibers of adjacent sensor units mutually converge to provide a contiguous imaging area free from inter-unit borders even where active imaging areas of contiguous sensor units do not extend up to the edges of the sensor units.

8. The sensor system as defined in claim 5, wherein the base unit comprises mechanical and electrical connections permitting the connection of said modular electronic control units via a first set of connectors to said base unit (80) and via a second set of connectors to their respective modular sensor units.

9. The sensor system as defined in claim 8, wherein:

said sensor system comprises a frame unit incorporating on one side an x-ray transmissive nontransparent protective cover with said modular sensor units placed end-to-end thereunder; and the side of said frame unit which is opposite to said protective cover (67) is provided with openings through which said modular sensor units are connected by means of said second set of connectors to their respective modular electronic control units.

10. The sensor as defined in claim 9, said modular sensor units are supported both longitudinally and laterally in place by means of support elements, of which support elements at least ones bracing the opposed sides of an adjacently mounted set of modular sensor units are provided with clamping members operative for fixing said sets of modular sensor units to said frame unit and aligning said sets of modular sensor units as required.

* * * * *